US005308347A

United States Patent [19]

Sunago et al.

[11] Patent Number: 5,308,347

[45] Date of Patent: May 3, 1994

[54] TRANSFUSION DEVICE

[75] Inventors: Seizo Sunago, Hyogo; Osamu Aoki, Osaka, both of Japan

[73] Assignee: Fujisawa Pharmaceutical Co., Ltd., Osaka, Japan

[21] Appl. No.: 944,401

[22] Filed: Sep. 14, 1992

[30] Foreign Application Priority Data

Sep. 18, 1991 [JP] Japan .................................. 3-238085

[51] Int. Cl.5 ........................ A61B 19/00; A61M 5/32; A61M 37/00

[52] U.S. Cl. .................................... 604/403; 604/408; 604/411; 604/416; 604/88

[58] Field of Search ................... 604/82, 88, 403, 408, 604/411–416, 905; 206/222

[56] References Cited

U.S. PATENT DOCUMENTS

D. 323,389 1/1992 Aoki et al. .
3,206,080 9/1965 Scislowicz .......................... 604/414
3,923,059 12/1975 Ogle .................................... 604/413
3,995,630 12/1976 van der Veerdonk ............. 604/416
4,583,971 4/1986 Bocquet et al. .
4,607,671 8/1986 Aalto et al. ...................... 604/416 X
4,886,495 12/1989 Reynolds ........................ 604/413 X
4,936,841 6/1990 Aoki et al. .......................... 604/413

FOREIGN PATENT DOCUMENTS 0341115 11/1989 European Pat. Off. .
8704649 9/1987 Fed. Rep. of Germany .
1019500 2/1966 United Kingdom ................ 604/416
8601712 3/1986 World Int. Prop. O. .......... 604/412
9300956 1/1993 World Int. Prop. O. .

*Primary Examiner*—C. Fred Rosenbaum
*Assistant Examiner*—Frank Wilkens
*Attorney, Agent, or Firm*—Oblon, Spivak, McClelland, Maier & Neustadt

[57] ABSTRACT

A transfusion device comprising a flexible vessel containing a solvent fluid, a drug container containing a drug, and a communicating portion for communicating the vessel and the container with each other, the commuicating portion comprising first and second passages adapted to communicate with the vessel and container and held in engagement with each other, a membrane and a plug member which are provided for closing the two communicating passages, and a particular cap held in thread engagement with the second communicating passage for enabling the two passages to communicate with each other.

When the vessel and the container are rotated relative to each other, the cap slides to disengage the plug member of the second communicating passage and break the membrane of the first communicating passage, thereby allowing the vessel and the container to communicate with each other.

5 Claims, 3 Drawing Sheets

TRANSFUSION DEVICE

BACKGROUND OF THE INVENTION

1. Field of the Invention

The present invention relates to a transfusion device, and more particularly to a transfusion device (container) used for drip infusion.

2. Description of the Prior Art

Hitherto, a drug in the form of powders or freeze-dried powders contained in a vessel such as a vial has been dissolved with a solvent and used as fluid for drip infusion in a medical organization such as a hospital. In that case, a vessel containing the drug is connected to a vessel containing a liquid for dissolving the drug by means of a connector such as a double-edged needle or communicating pipe.

The liquid for dissolving the drug is moved into the vessel containing the drug to dissolve the drug therewith.

Such procedure is, however, complicated and time consuming. Moreover, there is a possibility of the drug in the vessel being contaminated because a hole for connection is formed on the vessel containing the drug in the open air.

In order to solve the above mentioned problem, there has been proposed a transfusion device (container) as shown in Japanese Unexamined Patent Publication No. 61-501129 (which corresponds to U.S. Pat. No. 4,583,971).

As shown in FIG. 7, the transfusion device comprises a capsule (102) enclosing a vial (101), i.e., a drug container, and a flexible vessel (103) containing a liquid for dissolving a drug and having a fluid outlet, the capsule and the flexible vessel being connected to each other through a tube (104). In the tube (104), a hollow needle (105) is provided on the vial (101) side while a breaking member (106) is provided on the flexible vessel (103) side. The breaking member (106) closes a passage of the tube (104) and obstructs a flow of fluid.

In use, a cap (107) on the top of the capsule (102) is pushed with a finger to press down the vial (101). The needle (105) penetrates a rubber plug (108) of the vial (101) so that the flexible vessel (103) and the vial (101) are connected to each other. The breaking member (106) in the tube (104) is then bent with hands to open the passage of the tube (104) and to mix the drug and the liquid for dissolving the drug.

The above mentioned transfusion device has been improved in the point that mixing procedure is performed by communicating a drug container to a flexible vessel containing a liquid for dissolving the drug. The mixing procedure is still troublesome because a passage must be opened by bending the breaking member (106) with hands after sticking the rubber plug (108) of the vial (101) with the needle(105). Moreover, when the bending of the breaking member (106) is incomplete, fluid is hard to pass through the tube so that it takes much time to carry out the dissolution of the drug. In addition, the number of parts is relatively large and this results in high cost.

SUMMARY OF THE INVENTION

The present invention was made to eliminate the above mentioned drawbacks, and is intended to provide a transfusion device which is simple in construction and permits sure and easy communication between a drug container and a vessel of a liquid for dissolving a drug (which liquid is hereinafter referred to as a solvent fluid), and which enables the drug and solvent fluid to be mixed in short time and is low in cost.

According to the present invention there is provided a transfusion device comprising a flexible vessel containing a solvent fluid, a drug container containing a drug, and a communicating portion for communicating the drug container and the flexible vessel with each other, wherein the communication portion includes a first communicating passage leading to the interior of the flexible vessel integrally through an upper portion thereof, a membrane for closing the first communicating passage, a second communicating passage leading to the interior of the drug container integrally through a lower portion thereof and rotatably fitted in the inner side of said first communicating passage, a plug member for releasably plugging a lower port of the second communicating passage, and a cap threadedly engaging the lower outer periphery of said second communicating passage to hold said plug member and having a puncturing needle for puncturing said membrane, said cap being adapted to slide only axially along the inner periphery of the first communicating passage, whereby the cap can axially slide downward through relative rotational movement of the flexible vessel and the drug container to disengage said plug member and to cause said puncturing needle to puncture said membrane, thereby bringing the drug container and the flexible vessel into communication with each other.

In the device of the invention, the drug container and the flexible vessel are connected together by a particular communicating portion so that the container and the vessel through the relative rotational movement can be caused to internally communicate with each other, whereby the drug and the solvent fluid can be mixed for preparation of a transfusion liquid.

To cause the container and the vessel to internally communicate with each other, the two are rotated relative to each other. Following this rotation the cap first slides axially downward and then the plug member is disengaged to break the membrane through the puncturing needle. Thus, the interior of the drug container and the interior of the flexible vessel are allowed to communicate with each other.

In essence, the invention makes it possible to prepare a transfusion liquid in an accurate manner simply by bringing the drug container and the flexible vessel into relative rotation.

DESCRIPTION OF THE PREFERRED EMBODIMENTS

The invention will now be described in further detail with reference to an embodiment shown in FIG. 1. It is understood, however, the invention is not limited by the embodiment.

Figure 1:
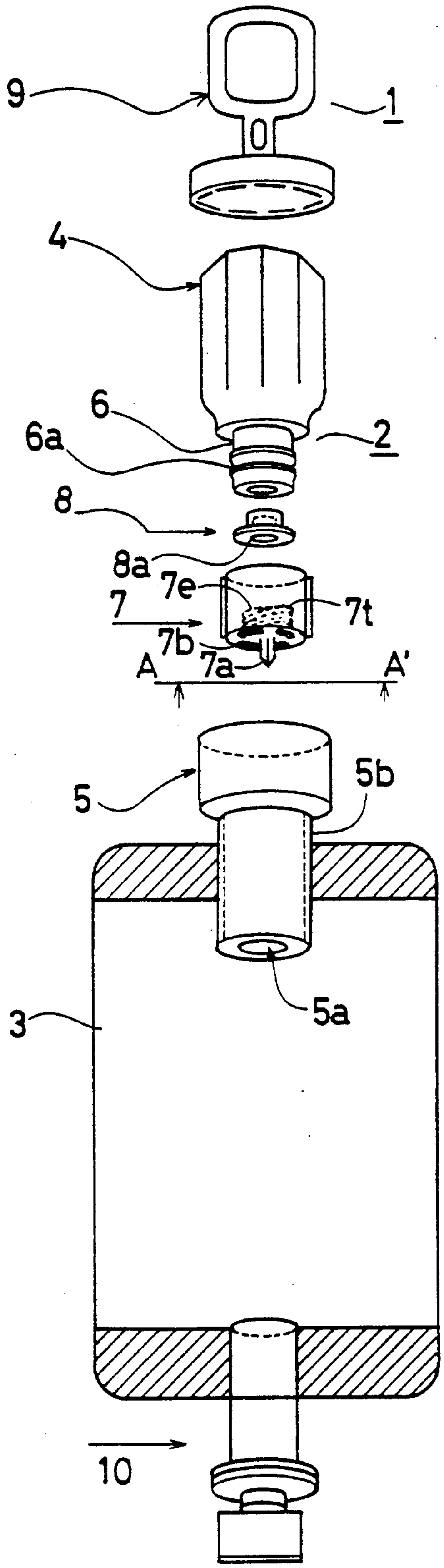
FIG. 1 is a perspective view showing various parts in one embodiment of the invention.

In FIG. 1, a transfusion device (container) (1) comprises a flexible vessel in the form of a bag (3) which contains therein a solvent fluid in sterilized condition, a drug vial (hereinafter referred to as a vial) (4), as a drug container, which contains therein a solid drug in sterilized condition, and a communicating portion (2) for allowing the vial (4) and the bag (3) to communicate with each other. The reference numeral (9) denotes a suspension member made of a soft polypropylene resin which is provided on the top of the vial (4). The reference numeral (10) denotes a fluid outlet provided in a lower portion of the bag (3).

The bag (3) is made of a flexible material, such as a soft vinyl chloride resin, a polyolefin resin or an ethylene vinyl acetate coplolymer. For use as such a material, a polyolefin resin is preferred because it has good chemical resistance and is little likely to be eluted in the solvent fluid.

Examples of solvent fluids suitable for being contained in the bag (3) include a physiological saline solution, a 5% glucose solution, distilled water for infusion, and also a solution containing various electrolytes.

The vial (4) (container body) is made of glass and contains a solid drug therein.

Examples of drugs which may be contained in the vial (4) include antibiotics, antitumer agents, and antiulcer agents.

Examples of antibiotics include cephem antibiotics, such as cefazolin sodium, ceftizoxime sodium, cefotiam dihydrochloride, cefmenoxime hemihydrochloride, cephacetrile sodium, cefamandole sodium, cephaloridine, cefotaxime sodium, cefotetan sodium, cefoperazone sodium, cefsulodin sodium, ceftezole sodium, cefpiramide sodium, cefmetazole sodium, and cefuroxime sodium; and penicillin antibiotics, such as ampicillin sodium, carbenicillin disodium, sulbenicillin disodium, and ticarcillin sodium. Examples of antitumor agents include mitomycin C, fluorouracil, tegafur, and cytarabine. Examples of antiulcer agents include famotidine, ranitidine hydrochloride, and cimetidine.

The communicating portion (2) consists essentially of a first communicating passage (5) leading to the interior of the bag (3) through a top portion thereof integrally therewith, a second communicating passage (6) leading to the interior of the vial (4) through a lower portion thereof integrally therewith, a rubber plug (8) serving as a closure for the second communicating passage (6), and a cap (7) operative to deplug the rubber plug (8) and to break a membrane (5*a*) closing the first communicating passage (5) which will be described hereinafter. These parts are shown as assembled together in FIG. 2. Reference numeral (11) designates a ring packing (o-ring), and (12) designates a connecting portion. Assembling of these parts is performed in a sterile room.

The first communicating passage (5) is closed by a membrane (5*a*) formed integrally with the lower port of the passage, and is provided on the inner periphery thereof with longitudinal grooves (5*b*) in which are fitted longitudinal ledge-like guides (7*c*) of the cap (7) to enable the cap (7) to slide axially while preventing it from turning.

The second communicating passage (6) has its lower port fitted with the rubber plug (8) and is externally threaded (right-hand threaded) (6*a*) on its periphery for thread engagement with the cap (7).

The first communicating passage (5) and the second communicating passage (6) have a common connecting portion (12) by which they are coupled to each other for relative rotation in such a condition that the second communicating passage (6) is fitted in the first communicating passage (5).

The cap (7) has puncturing needle (7*a*) for puncturing the membrane (5*a*) which is located centrally of the outer side of the bottom plate of the cap. The bottom plate is formed with arcuate slits (7*b*) around the needle (7*a*) for enabling the movement of the liquid when communication is effected between the bag and vial.

The cap (7) is provided on its outer periphery with longitudinal ledge-like guides (7*c*) for preventing the first and second communicating passages from turning in association with each other, and is internally threaded (right-hand threaded) (7*d*) on its periphery for thread engagement with the second communicating passage (6). The cap (7) has a boss (7*e*) located centrally of the inner side of the bottom plate, the boss (7*e*) being externally threaded (left-hand threaded) (7*f*) on its periphery for thread engagement with a bottom hole (8*a*) of the rubber plug (8) to be pulled out therewith.

Nextly, the method of using the transfusion device (1) constructed as described above will be explained.

Figure 2:
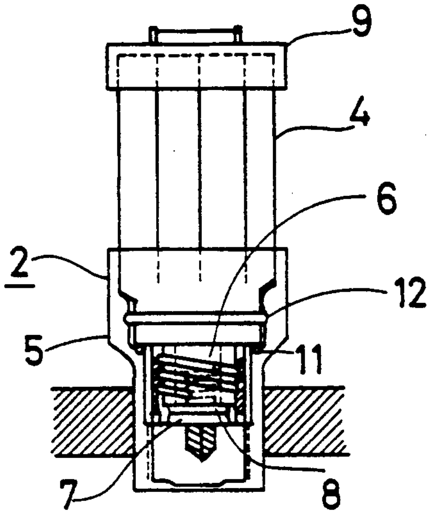
FIG. 2 is a sectional view showing a communicating portion in assembled form.

In FIG. 2, when the vial (4) is rotated relative to the bag (3), the cap (7) moves axially downward without rotation because the longitudinal grooves (5*b*) of the first communicating passage (5) are held in engagement with the longitudinal ledge-like guides (7*c*) of the cap (7), and thus the cap (7) is finally disengaged from the second communicating passage (6). In this case, the rubber plug (8) which is in thread engagement with the cap (7) is disengaged from the second communicating passage (6) in conjunction with the cap (7), without becoming separated therefrom, because it is left-hand thread engagement (left-hand threaded) (7*f*) with the cap.

Figure 3:
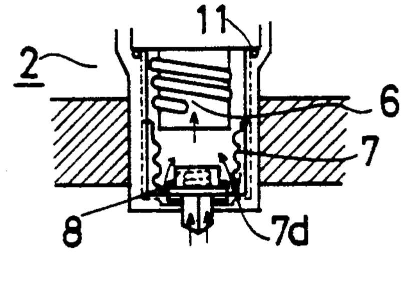
FIG. 3 is a sectional view showing the communicating portion in assembled form as brought in the state of interpassage communication.
Figure 4:
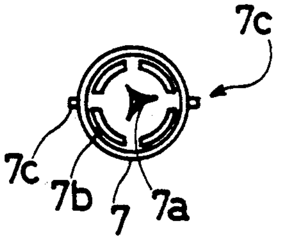
FIG. 4 is a view of cap (7) as taken in the direction of the arrows along the line A - A' in FIG. 1.
Figure 7:
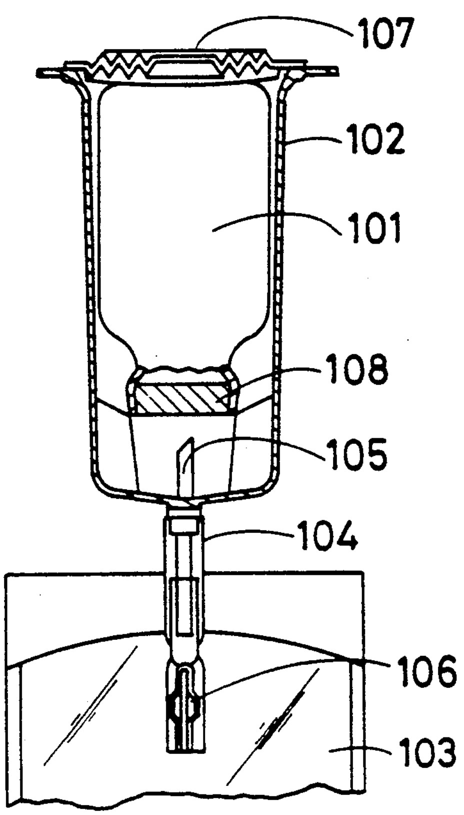
FIG. 7 is a front view, partly in section, showing a prior art arrangement.

When such relative rotation is further continued, the puncturing needle (7*a*) of the cap (7) breaks the membrane (5*a*) of the first communicating passage (5) and thus the interior of the vial (4) goes into communication with the interior of the bag (3). FIG. 3 shows the vial and the bag as brought in communication with each other. In the figure, arrows indicate the path of solvent fluid flow.

Intermittent compression is applied to the bag (3) to cause the solvent fluid in the bag (3) to move through the arcuate slits (7*b*) to the vial (4) and back therefrom, thereby to dissolve the drug in the vial (4). Thus, a uniform transfusion fluid can be obtained in the fluid transfusion device (1), namely an interconnected assembly of vial (4) and bag (3).

As stated above, the fluid transfusion device (1) has a smaller number of parts and is less expensive, and enables preparation of infusion liquid more easily in short time simply by turning the vial (4) and bag (3) relative to each other.

Figure 5:
FIG. 5 is a perspective view showing a seal disk (13) in another embodiment.

In another embodiment, a seal disk (13) of such a configuration as shown in FIG. 5 may be used as a closure for the second communicating passage, and a cap (14) (not shown) which is different from the cap (7) shown in FIG. 1 in that it has neither boss (7*e*) nor external thread (7*f*) may be used as such. The seal disk

Figure 6:
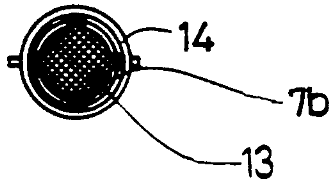
FIG. 6 is a plan view of another embodiment in which a seal disk (13) and a cap (14) are shown as fitted together by adhesion.

(13) is fitted or attached by adhesion to the bottom plate portion of the cap (14) at the inner side thereof so as not to block the arcuate slits (7b), as shown in FIG. 6. The cap is threadingly fitted on the lower outer periphery of the second communicating passage (6) to close the lower port of the second communicating passage (6).

Then, in same manner as in the case of the foregoing embodiment, relative rotation is effected, whereby the cap (14), accompanied by the seal disk (13), is disengaged from the second communicating passage (6) to render the second communicating passage (6) free to communicate. When such operation for relative rotation is further continued, the first communicating passage (5) is rendered free to communicate in same manner as in the foregoing embodiment. Thus, the vial and the bag are made free to communicate with each other.

According to the invention, easy and very positive communication between containers can be achieved and, in addition, fewer parts are required and costs involved can be reduced.

What is claimed is:

1. A transfusion device comprising a flexible vessel containing a solvent fluid, a drug container containing a drug, and a communicating portion for communicating the drug container and the flexible vessel with each other;

wherein the communicating portion includes a first communicating passage leading to the interior of the flexible vessel integrally through an upper portion thereof, a membrane for closing the first communicating passage, a second communicating passage leading to the interior of the drug container integrally through a lower portion thereof, a plug member for releasably plugging a lower port of the second communicating passage, and a cap including a threaded peripheral portion engaging a threaded periphery of said second communicating passage said cap having a puncturing needle for puncturing said membrane, wherein at least one of said cap and said first communicating passage includes a guide member which restrains rotational movement of said cap such that relative rotation between said drug container and said flexible vessel causes said cap to move axially with respect to said first communication passage with said cap thereby movable along a path within said first communicating passage, said path including a first position at which said puncturing needle is spaced from said membrane, and wherein said plug member is disposed between an end of said cap and an interior of said drug container such that in said first position said cap holds said plug to close said lower port of the second communicating passage, said path further including a second position at which said puncturing needle extends through said membrane;

whereby the cap moves along said path from said first position to said second position by relative rotational movement of the flexible vessel and the drug container to disengage said plug member and to cause said puncturing needle to puncture said membrane, thereby bringing the drug container and the flexible vessel into communication with each other.

2. The transfusion device of claim 1, wherein said plug member is a disk mounted adjacent an interior bottom plate portion of said cap.

3. The transfusion device of claim 1, wherein said plug member is connected to a boss, said boss located on an inner surface of said cap.

4. The transfusion device of claim 1, wherein a pair of said guide members are provided extending along said cap in an axial direction of said cap, and wherein said first communicating passage includes a pair of grooves respectively receiving said guide members such that engagement of said guide members within said grooves prevents rotational movement of said cap as said drug container and said flexible vessel are rotated relative to one another.

5. A transfusion device comprising a vessel containing a solvent fluid, a container containing a drug, and a communicating portion for communicating the container and the vessel with each other;

said communicating portion including a first communicating passage extending into said vessel through an upper portion thereof, said first communicating passage including a membrane extending across a portion of said first communicating passage for closing the first communicating passage, said container including a second communicating passage, said second communicating passage including a threaded outer peripheral portion;

a cap including a threaded internal portion for threaded engagement with the threaded outer peripheral portion of said second communicating passage, wherein said cap and said second communicating passage are disposed within said first communicating passage, said cap further including a puncturing member, and wherein a plug member is mounted within an interior of said cap such that when said cap is screwed onto said second communicating passage by said threaded engagement said plug is disposed in a sealing position to close said second communicating passage and said puncturing member is spaced from said membrane, and when said cap is unscrewed from said second communicating passage said plug is spaced from said second communicating passage; and wherein a ledge is disposed on one of an outer periphery of said cap and an inner periphery of said first communicating passage, and a groove is provided on the other of said outer periphery of said cap and an inner periphery of said first communicating passage, said ledge disposed within said groove such that rotational movement of said cap with respect to said first communicating passage is restrained, whereby rotational movement of said container with respect to said vessel causes axial movement of said cap along said first communicating passage as the cap is unscrewed from said second communicating passage such that said plug is removed from said sealing position with respect to said second communicating passage and said puncturing member penetrates said membrane.

* * * * *